United States Patent [19]

Mueller et al.

[11] Patent Number: 4,736,030

[45] Date of Patent: Apr. 5, 1988

[54] PREPARATION OF 1-ALKYL- OR 1-CYCLOALKYLPIPERAZINES

[75] Inventors: Herbert Mueller, Frankenthal; Dieter Voges, Mannheim; Wolfgang Lengsfeld, Limburgerhof, all of Fed. Rep. of Germany

[73] Assignee: BASF Aktiengesellschaft, Ludwigshafen, Fed. Rep. of Germany

[21] Appl. No.: 791,112

[22] Filed: Oct. 24, 1985

[30] Foreign Application Priority Data

Nov. 3, 1984 [DE] Fed. Rep. of Germany ....... 3440195

[51] Int. Cl.$^4$ .................. C07D 405/04; C07D 295/02
[52] U.S. Cl. .................... 544/374; 544/358; 544/403; 544/404
[58] Field of Search ................ 544/358, 403, 404, 374

[56] References Cited

U.S. PATENT DOCUMENTS

| | | | |
|---|---|---|---|
| 2,058,547 | 10/1936 | Adkins et al. | 546/184 |
| 2,639,284 | 5/1953 | Morren | 544/357 |
| 3,948,900 | 4/1976 | Moss | 544/404 |
| 4,105,657 | 8/1978 | Dockner | 544/404 |
| 4,152,353 | 5/1979 | Habermann | 564/364 |
| 4,207,263 | 6/1980 | Hoffmann et al. | 564/480 |
| 4,242,343 | 12/1980 | Najer et al. | 544/374 |
| 4,267,175 | 5/1981 | Watts | 544/374 |

FOREIGN PATENT DOCUMENTS

| | | |
|---|---|---|
| 0034480 | 2/1961 | European Pat. Off. . |
| 2205597 | 12/1977 | Fed. Rep. of Germany . |
| 153371 | 1/1982 | Fed. Rep. of Germany . |
| 22772 | 3/1981 | Japan .................. 544/374 |
| 1030310 | 5/1966 | United Kingdom . |

OTHER PUBLICATIONS

Baltzly et al., JACS, vol. 66, pp. 263–266.
Dockner et al., Chem. Abst., 79-115626g.
W. Gelger and H. Rase, Useful Products from Piperazine, Methylpiperazines and an Amorphous Dibasic Acid/Piperazine Polymer, Ind. Eng. Chem. Prod. Res. Dev., 1981, 20, 688–693.
Journal of Organic Chemistry, 21, 86, (1956).

*Primary Examiner*—Donald G. Daus
*Assistant Examiner*—Cecilia Shen
*Attorney, Agent, or Firm*—Keil & Weinkauf

[57] ABSTRACT

1-Alkyl- or 1-cycloalkylpiperazines are prepared by reacting piperazine with an alkanol or cycloalkanol in the presence of hydrogen and a hydrogenation/dehydrogenation catalyst by a process in which the reaction is carried out at from 130° to 190° C. under from 5 to 100 bar in the presence of from 5 to 40% by weight, based on the reaction mixture, of water, and the molar ratio of piperazine to alkanol or cycloalkanol is kept at from 1:1.5 to 1:8.

6 Claims, No Drawings

PREPARATION OF 1-ALKYL- OR 1-CYCLOALKYLPIPERAZINES

The present invention relates to a novel process for the preparation of 1-alkyl- or 1-cycloalkylpiperazines by reacting piperazine with an alkanol or cyclo-alkanol in the presence of a hydrogenation/dehydrogention catalyst and hydrogen.

DE-B-2 205 597 proposes the preparation of the N-alkyl derivatives of morpholine, piperazine, piperidine, hexamethyleneimine or pyrrolidine by alkylation with an aliphatic hydroxy compound or one of its ethers under atmospheric pressure in the presence of a dehydration catalyst based on silica. In the case of piperazine, however, complete conversion does not take place.

EP-A-34 480 describes the preparation of N-alkylamines or N,N-dialkylamines by means of special catalysts which are based on triphenylphosphine complexes of the metals indium, rhodium, ruthenium, osmium, platinum, palladium and rhenium. One of the possible starting materials stated is piperazine.

According to U.S. Pat. No. 4,152,353, alcohols, aldehydes or ketones are supposed to react with aminating reagents in the presence of a catalyst containing nickel and copper to give amines. Preferably used aminating agents are ammonia and primary amines. The use of, among other substances, piperazine as an aminating agent is mentioned in the description.

In the process described there, however, a minimum molar ratio of aminating reagent to alcohol of from 1:1 to 5:1 must be maintained, and it is even preferable to use a molar ratio of 100:1.

Finally, J. Org. Chem. 21 (1956), 86 describes the preparation of N-alkyl-substituted piperazines starting from, inter alia, piperazine and lower.alkanols in the presence of a nickel catalyst in an autoclave. The molar ratio of piperazine to alkanol is from 1:25 to 1:36. However, the resulting yields of N-monoalkyl- and N,N'-dialkyl-substituted piperazines are very unsatisfactory in this case.

It is an object of the present invention to provide a process which permits virtually complete conversion of the piperazine used and at the same time reduces the formation of 1,4-dialkylpiperazines to an acceptably low level, since 1-alkylpiperazines.are extremely difficult to work up in the presence of unconverted piperazine.

We have found that this object is achieved, and that 1-alkyl- or 1-cycloalkylpiperazines are advantageously obtained by reacting piperazine with an alkanol or cycloalkanol in the presence of hydrogen and a hydrogenation/dehydrogenation catalyst, if the reaction is carried out at from 130° to 190° C. and under from 5 to 100 bar in the presence of from 5 to 40% by weight, based on the reaction mixture, of water, and the molar ratio of piperazine to alkanol or cycloalkanol is maintained at from 1:1.5 to 1:8.

This result is surprising since it could not be foreseen that the 97-100% piperazine conversion necessary for working up by distillation would be achieved under the stated conditions.

It was also not to be expected that, in spite of a large excess of alkanol or cycloalkanol, the desired monoalkylated products, i.e. 1-alkyl or 1-cycloalkylpiperazines, would be formed with good selectivity (in general from 60 to 90%).

The novel process takes place in the presence of hydrogenation/dehydrogenation catalysts. Suitable catalysts for carrying out the reaction contain the metals conventionally employed for hydrogenation/dehydrogenation catalysts, for example copper or metals of group 8 of the Periodic Table of Elements, such as iron, cobalt, nickel, palladium or platinum.

The catalysts can be prepared by a conventional method, for example by impregnation of a carrier, such as silica gel, alumina, pumice or bleaching earth, with the corresponding aqueous salt solutions, followed by drying, calcination and reduction. They may also be prepared by the coprecipitation method. Carrier-free catalysts, e.g. Raney metals, are also suitable for the process. The catalysts are used in the form of a fixed bed or as a suspension.

A hydrogenation/dehydrogenation catalyst based on nickel is preferably used, Raney nickel in suspended form being particularly preferred. The best results in terms of both cost efficiency of the process and its selectivity are obtained when nickel catalysts are used.

The alkylating agents used are alkanols or cycloalkanols.

Preferably used alkanols are those of 1 to 10, in particular 2 to 6, carbon atoms, e.g. methanol, ethanol, propanol, isopropanol, butanol, isobutanol, hexanol, octanol or 2-ethylhexanol.

Preferably used cycloalkanols are compounds having 3 to 12 carbon atoms in the molecule, e.g. cyclopropanol, cyclopentanol, cyclohexanol, 2-methylcyclohexanol, 4-ethylcyclohexanol or cyclododecanol.

The molar ratio of piperazine to alkanol or cycloalkanol is from 1:1.5 to 1:8, preferably from 1:2 to 1:5. No further advantages are obtained by carrying out the process using a molar ratio greater than 1:8. In this case, an increase in the amount of 1,4-dialkyl- or 1,4-dicycloalkylpiperazines is observed.

The process according to the invention is carried out at from 130° to 190° C., preferably from 140° to 180° C., under from 5 to 100, preferably 20 to 80, bar. A distinction should be made between a lower pressure range of from 5 to 65, preferably from 20 to 65, bar and an upper pressure range of from 65 to 100, preferably from 65 to 80, bar.

According to the invention, the reaction is effected in the presence of hydrogen, the stated total pressure essentially being determined by the partial pressure of the hydrogen. Thus, the alkylation of the piperazine is carried out in the presence of hydrogen in an amount sufficient to establish a pressure within the stated range.

If the reaction is effected under a pressure within the upper range, a lower temperature is required than for the lower pressure range. As a rule, a temperature of from 140° to 170° C. is sufficient in this case.

Although the novel process may be carried out under above 100 bar, this pressure range does not result in any further advantages.

The novel process is carried out in the presence of from 2 to 40% by weight, based on the reaction mixture, of water. If the water content is lower than 2% by weight, the selectivity achievable is markedly reduced. When the water content is increased to above 40% by weight, the reaction is slowed down without a higher selectivity being achieved.

In some cases, the alkylation of amines with alcohols should be carried out in the absence of water in order to achieve a high conversion and a high reaction rate. For example, in the preparation of a tertiary amine from a secondary amine and an alcohol, the water formed during the reaction is removed, at the rate at which it is formed, from the liquid reaction mixture (cf. DE-A-2645712).

In contrast to this rule, the process according to the invention takes place in the presence of water at a higher reaction rate and with better selectivity. From an economic standpoint, this advantage of the process should not be underestimated. Piperazine is a solid compound which, for reasons of occupational hygiene, is not easy to handle. According to the invention, however, the fluid aqueous piperazine solutions can be employed just as successfully as solid piperazine; hence, the alkylation process is particularly economical.

In a preferred embodiment of the novel process, the conversion of the piperazine is carried out in the presence of from 0.01 to 1, preferably from 0.01 to 0.1, % by weight, based on the reaction mixture, of an inorganic base.

Inorganic bases used are the compounds derived from the alkali metals or alkaline earth metals, such as the oxides, hydroxides or carbonates. Examples of suitable compounds are sodium hydroxide, potassium hydroxide, sodium carbonate, sodium bicarbonate, calcium hydroxide and calcium oxide.

Of course, several of the stated compounds may be present simultaneously during the reaction. Alkali metal carbonates are preferred. The bases can be used in solid or powdered form or in the form of, for example, concentrated solutions, together with the hydrogenation/dehydrogenation catalysts.

As described above, the alcohol is used in excess in the process according to the invention. Consequently, when the reaction is carried out on an industrial scale, some of the alkanol or cycloalkanol used is advantageously circulated. The azeotrope obtained in the separation of the particular alcohol from the desired product by distillation can subsequently be recycled directly to the process without an expensive drying procedure.

The novel process can be carried out continuously or batchwise.

The starting materials piperazine, preferably in the form of its aqueous solution, and the alcohol and, if required, the inorganic base are mixed, and the mixture is fed to the particular catalyst system and reacted in the presence of hydrogen.

The reaction can in principle also be carried out in the presence of a water-miscible solvent which is inert under the reaction conditions, for example tetrahydrofuran, dioxane or ethylene glycol dimethyl ether.

The measure usually taken when alkylating amines with alcohols, i.e. continuously removing the water formed during the reaction, can be dispensed with in the present case.

We have also found that the selectivity of the conversion of piperazine to 1-alkyl- or 1-cycloalkylpiperazines also depends partly on the catalyst concentration. If the amount of catalyst falls below the critical minimum amount, the selectivity decreases substantially, regardless of the reaction rate. A decrease in selectivity is also observed when the catalyst concentration is too high.

The critical minimum concentration of catalyst is determined by its specific activity, so that it is difficult to give a general value. However, it may be stated that, for example where suspended Raney nickel is used, the critical catalyst concentration is about 0.2–1% by weight, based on the reaction mixture. Commercial Raney nickel is advantageously used in a concentration of from 2 to 5% by weight, based on the reaction mixture.

When the reaction is complete, the catalyst can be separated off by, for example, filtration, centrifuging or sedimentation and can be used for many further reactions. If this procedure is used, the catalyst unit ratio can readily be reduced to below 0.1%.

In the continuous mode of operation over a fixed-bed catalyst, an appropriate method must be used to ensure that a certain space velocity (kg of reactants per 1 of catalyst volume per unit time) is not exceeded, since otherwise the selectivity of the reaction is reduced. The space velocity is also dependent on the catalyst used and has to be determined for each individual case. For example, a commercial supported nickel catalyst having a magnesium silicate carrier and containing about 50% by weight, based on the catalyst, of nickel has a limiting space velocity of about 0.5 kg of reactants per 1 of catalyst per hour. The necessary minimum residence time (or maximum space velocity of the catalyst) is most simply determined by finding the extent to which these parameters can be reduced, starting from a given value, without adversely affecting the result obtained in the process (i.e. the selectivity).

When the measures described are taken, the piperazine used can be virtually completely converted using the novel process.

This aspect is particularly important in the synthesis of N-alkylpiperazines containing a lower alkyl radical ($C_1$–$C_6$), since unconverted piperazine, or piperazine which may be present in excess, is very difficult to separate off during working up of the reaction mixtures formed in this case. In particular, the water present, which is formed during the reaction or may also have been present in a certain amount from the beginning, interferes with the distillative working up procedure. In this case, complicated azeotropes, some of which contain several components, are formed between piperazine, monoalkylpiperazine and dialkylpiperazine.

If, on the other hand, complete conversion of the piperazine takes place, it is only necessary to separate the monoalkylated piperazine (desired product) from the dialkylated piperazine (by-product) during working up by distillation, and the particular desired products are obtained in high purity.

The stated 1-alkyl- and 1-cycloalkylpiperazines are useful intermediates, for example for the synthesis of active ingredients or dyes.

The Examples which follow illustrate the invention. Parts are by weight, and parts by weight bear the same relation to parts by volume as that of the kilogram to the liter.

EXAMPLE 1

250 parts of water-moist Raney nickel containing 30% by weight of water were added to a mixture of 1400 parts of piperazine, 950 parts of water and 3128 parts of ethanol, and the stirred mixture was reacted in a pressure vessel under a hydrogen pressure of 60 bar and at 175° C. for 10 hours. No absorption of hydrogen was observed. The pressure vessel was cooled and the pressure then let down. The reaction mixture was then decanted, freed from residual catalyst and analyzed. Distillation under 1 mbar and at 180° C. showed that less than 0.5% by weight, based on the anhydrous reaction product, of nonvolatile by-products had formed. The product consisted of 0.8% by weight of unreacted piperazine, 55% by weight of ethylpiperazine, 43% by weight of 1,4-diethylpiperazine and 1.5% by weight of unidentified substances (without taking into account water and ethanol). Fractional distillation gave 1-ethylpiperazine having a purity of 99.5% by weight.

EXAMPLE 2

A procedure similar to that described in Example 1 was followed, except that 1.5 parts of sodium carbonate were also added to the reaction mixture together with the Raney nickel. In this case, the reaction was complete after as short a time as 5 hours. The content of 1-ethylpiperazine in the reacted mixture was 75% by weight (without taking into account water and ethanol). The amount of high-boiling products obtained decreased to the region of the detection limit. The water-containing alcohol azeotrope which was obtained in this reaction, as in the above reaction, and which was redistilled could be used for further reactions without further purification. The catalyst which settled out could also be reused and did not show any decrease in reactivity, even after being employed 20 times, if 1% by weight of the amount of alkali metal salt originally introduced was added to each batch.

Similar results were obtained when 2 parts of calcium hydroxide were used instead of sodium carbonate.

EXAMPLE 3

A procedure similar to that described in Example 1 was followed, except that the reaction was carried out in the presence of 0.5% by weight, based on the reaction mixture, of calcium hydroxide, using 5032 parts of butanol instead of ethanol. After 5 hours, 1-butylpiperazine was obtained in a yield of 70% by weight and 1,4-dibutylpiperazine in a yield of 29.5% by weight, the percentages being based on the reacted mixture freed from water and butanol.

EXAMPLE 4

A procedure similar to that in Example 1 was followed, except that the reaction was carried out in the presence of one part of potassium carbonate, using an equivalent amount of 3-hydroxymethyltetrahydrofuran instead of ethanol. After 10 hours, 74% by weight of 1-piperazinyl-3-tetrahydrofuranylmethane and 25% by weight of the disubstituted piperazine compound were obtained.

We claim:

1. A process for the preparation of a 1-alkyl-, 1-cycloalkylpiperazine or 1-piperazinly-3-tetrahydrofuranylmethane by reacting piperazine with an alkanol, cycloalkanol or 3-hydroxymethyltetrahydrofuran in the presence of hydrogen and a hydrogenation/hydrogenation catalyst, wherein the reaction is carried out at from 130° to 190° C. and under from 5 to 100 bar in the presence of from 5 to 40% by weight, based on the reaction mixture, of water which is added to the reaction mixture, and in the presence of from 0.01 to 1% by weight, based on the reaction mixture, of an inorganic base, and the molar ratio of piperazine to alkanol, cycloalkanol or 3-hydroxymethyltetrahydrofuran is kept at from 1:1.5 to 1:8.

2. The process of claim 1, wherein hydrogenation/-dehydrogenation catalyst based on nickel is used.

3. The process of claim 1, wherein an alkanol of 1 to 10 carbon atoms is used.

4. The process of claim 3, wherein the alkanol is methanol, ethanol, propanol, isopropanol, butanol, isobutanol, hexanol, octanol or 2-ethylhexanol.

5. The process of claim 1, wherein the inorganic base is selected from the group consisting of sodium hydroxide, potassium hydroxide, sodium carbonate, sodium bicarbonate, calcium hydroxide and calcium oxide.

6. The process of claim 1, wherein the inorganic base is sodium carbonate or calcium hydroxide.

* * * * *